United States Patent
Vora et al.

(10) Patent No.: US 9,919,983 B2
(45) Date of Patent: Mar. 20, 2018

(54) PROCESSES AND APPARATUSES FOR PRODUCTION OF POLYPROPYLENE

(71) Applicant: UOP LLC, Des Plaines, IL (US)

(72) Inventors: Bipin V. Vora, Naperville, IL (US); Hayim Abrevaya, Kenilworth, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 15/609,465

(22) Filed: May 31, 2017

(65) Prior Publication Data

US 2017/0369389 A1 Dec. 28, 2017

Related U.S. Application Data

(60) Provisional application No. 62/353,480, filed on Jun. 22, 2016.

(51) Int. Cl.
| | |
|---|---|
| *C07C 1/24* | (2006.01) |
| *C07C 1/20* | (2006.01) |
| *C07C 2/18* | (2006.01) |
| *C07C 4/04* | (2006.01) |
| *C07C 5/333* | (2006.01) |

(52) U.S. Cl.
CPC .............. *C07C 1/20* (2013.01); *C07C 2/18* (2013.01); *C07C 4/04* (2013.01); *C07C 5/333* (2013.01); *C07C 2527/173* (2013.01); *C07C 2529/85* (2013.01)

(58) Field of Classification Search
CPC ........ B01J 29/85; B01J 2229/42; B01J 29/90; B01J 2229/26; B01J 29/18; B01J 2229/36; B01J 29/84; B01J 2229/16; B01J 23/74; B01J 29/40; B01J 29/65; B01J 29/70; B01J 2229/40; B01J 37/0045; C07C 1/20; C07C 11/02; C07C 2529/85; C07C 2529/40; C07C 4/06; C07C 1/24; C07C 1/207; C07C 1/26; C07C 1/322; C07C 1/323; C07C 7/163; C07C 11/04; C07C 11/06; C07C 11/20; C07C 2/00; C10G 3/49; C10G 2400/20; C10G 2300/1011; C10G 2300/1081; C10G 2300/807; C10G 2400/02; C10G 2400/30; C10G 3/60; C10G 3/62
See application file for complete search history.

(56) References Cited

U.S. PATENT DOCUMENTS

| | | |
|---|---|---|
| 3,928,483 A | 12/1975 | Chang et al. |
| 4,025,575 A | 5/1977 | Chang et al. |
| 4,447,669 A | 5/1984 | Hamon et al. |
| 4,496,786 A | 1/1985 | Santilli et al. |
| 4,499,314 A | 2/1985 | Seddon et al. |
| 4,547,616 A | 10/1985 | Avidan et al. |
| 4,677,242 A | 6/1987 | Kaiser |
| 4,843,183 A | 6/1989 | Inui |
| 4,861,938 A | 8/1989 | Lewis et al. |
| 4,973,792 A | 11/1990 | Lewis et al. |
| 5,095,163 A | 3/1992 | Barger |
| 5,126,308 A | 6/1992 | Barger et al. |
| 5,191,141 A | 3/1993 | Barger et al. |
| 5,914,433 A | 6/1999 | Marker |
| 7,268,265 B1 | 9/2007 | Stewart et al. |
| 9,522,853 B2 * | 12/2016 | Adam ................ C07C 1/24 |

* cited by examiner

*Primary Examiner* — Sharon Pregler

(57) ABSTRACT

Processes and apparatuses for the production of propylene are provided. In an embodiment, a process is provided for production of propylene from an oxygenate feed comprising passing the oxygenate feed to an oxygenate-to-olefin reactor to contact the oxygenate feed with a catalyst to provide an effluent stream comprising olefins comprising ethylene, propylene and butylene. The effluent stream is separated in a product separation zone to generate a propylene product stream, an ethylene stream and a $C_4+$ stream. The ethylene stream is reacted in an ethylene dimerization or oligomerization reactor in presence of a dimerization or oligomerization catalyst to provide a first process stream. The $C_4+$ stream and the first process stream are cracked in a cracking reactor under cracking conditions to provide a cracked stream comprising additional amounts of ethylene and propylene. Finally, the cracked stream is passed to the product separation zone to recover additional amounts of propylene.

20 Claims, 3 Drawing Sheets

PROCESSES AND APPARATUSES FOR PRODUCTION OF POLYPROPYLENE

CROSS-REFERENCE TO RELATED APPLICATION

This application claims priority from Provisional Application No. 62/353,480 filed Jun. 22, 2016, the contents of which cited application are hereby incorporated by reference in its entirety.

TECHNICAL FIELD

The technical field generally relates to a processes for the production of light olefins from an oxygenate feedstream. More particularly, the technical field relates to processes and apparatuses for maximizing propylene production in a oxygenate to olefin process.

BACKGROUND

Light olefin materials, including ethylene and propylene, represent a large portion of the worldwide demand in the petrochemical industry. Specifically, propylene demand in the petrochemical industry has grown substantially, largely due to its use as a precursor in the production of polypropylene for packaging materials and other commercial products. Other downstream uses of propylene include the manufacture of acrylonitrile, acrylic acid, acrolein, propylene oxide and glycols, plasticizer oxo alcohols, cumene, isopropyl alcohol, and acetone.

Propylene is typically produced during the steam cracking or pyrolysis of hydrocarbon feedstocks such as natural gas, petroleum liquids, and carbonaceous materials (e.g., coal, recycled plastics, and organic materials), to produce ethylene. Additional sources of propylene are byproducts of fluid catalytic cracking (FCC) and reside fluid catalytic cracking (RFCC), normally targeting gasoline production. FCC is described, for example, in U.S. Pat. No. 4,288,688 and elsewhere. A mixed, olefinic $C_3/C_4$ hydrocarbon byproduct stream of FCC may be purified in propylene to polymer grade specifications by the separation of $C_4$ hydrocarbons, propane, ethane, and other compounds.

More recently, the desire for propylene and other light olefins from alternative, non-petroleum based feeds has led to the use of oxygenates such as alcohols and, more particularly, methanol, ethanol, and higher alcohols or their derivatives. Methanol, in particular, is useful in a methanol-to-olefin (MTO) conversion process described, for example, in U.S. Pat. No. 5,914,433. The yield of light olefins from such a process may be improved using olefin cracking to convert some or all of the $C_4$+ product of MTO in an olefin cracking reactor, as described in U.S. Pat. No. 7,268,265. Flexibility in the MTO product selection to integrate the MTO plant within the existing petrochemical infrastructure is a challenge while designing new plants. The MTO process produce significant amount of $C_4$ olefins, $C_5$ olefins, aromatics and heavier species in addition to ethylene and propylene which are the desirable products. The effective utilization of these by-products can result in increased production of light olefins such as propylene and ethylene and can significantly improve the economics of the process. Also, $C_4$ olefins may be used to provide other high value products such as butadiene.

In a typical MTO process employing SAPO-34, Propylene to Ethylene (P/E) product ratio at best can be 1.5. With the integration of Olefin cracking process (OCP), the P/E product ratio can be raised to about 2.0. Further, in an MTO process employing SAPO-18 and an operating pressure of 50 psig, the (P/E) product ratio is around 2:1 and with OCP integration (MTO-OCP) it can be raised between 2.5:1 to 3.0:1. Accordingly, under the best circumstances, with SAPO-18 and higher pressure in a MTO-OCP unit, the product composition will be 75% propylene and 25% ethylene.

However, there is a great demand for increase in propylene product specifically. The competitive route of Lurgi MTP® (methanol-to-propylene) process produces about 65% propylene, 25% gasoline $C_5$+ fraction and balance $C_4$- light ends. It is easier to sell byproduct gasoline than ethylene. It can be sent by rail car or truck to customer locations. For SAPO based MTO process, ethylene is not easy to transport, or the propylene producer also must get into ethylene derivative business and install an ethylene conversion process. This requires significant additional capital.

Another alternative is to install a $C_2$-$C_4$ olefin metathesis process plant and convert it to propylene. The catalyst for the metathesis process is very sensitive to impurities and MTO $C_4$ fraction will require extensive feed treatment. The process is also somewhat complex and requires significant more capital.

Accordingly, it is desirable to effectively utilize by-products in an MTO-OCP process for increased production of propylene and achieve higher P/E product ratio. Further, it is desirable to increase production of propylene in an oxygenate to olefin process with lower capital and operating cost requirements. Furthermore, other desirable features and characteristics of the present subject matter will become apparent from the subsequent detailed description of the subject matter and the appended claims, taken in conjunction with the accompanying drawings and this background of the subject matter.

BRIEF SUMMARY

Various embodiments contemplated herein relate to processes and apparatuses for maximizing the production of propylene in an oxygenate to olefin conversion process. The exemplary embodiments taught herein provide integration of ethylene oligomerization into an MTO-OCP for maximizing propylene production.

In accordance with an exemplary embodiment, a process is provided for production of propylene from an oxygenate feed comprising passing the oxygenate feed to an oxygenate-to-olefin reactor to contact the oxygenate feed with a catalyst comprising a silicoaluminophosphate (SAPO) to provide an effluent stream comprising olefins comprising ethylene, propylene and butylene. The effluent stream is separated in a product separation zone to generate a propylene product stream, an ethylene stream and a $C_4$+ stream. The ethylene stream is reacted in an ethylene dimerization or oligomerization reactor in presence of a dimerization or oligomerization catalyst to provide a first process stream. The $C_4$+ stream and the first process stream are cracked in a cracking reactor under cracking conditions to provide a cracked stream comprising additional amounts of ethylene and propylene. Finally, the cracked stream is passed to the product separation zone to recover additional amounts of propylene.

In accordance with another exemplary embodiment, a process is provided for the production of propylene from an oxygenate feed comprising passing the oxygenate feed to an oxygenate-to-olefin reactor to contact the oxygenate feed with a catalyst comprising a silicoaluminophosphate (SAPO) to provide an effluent stream comprising olefins comprising ethylene, propylene and butylene. The effluent stream is separated in a product separation zone to provide a propylene product stream, an ethylene stream, $C_4$ olefin stream and a $C_5+$ olefin stream. The ethylene stream is reacted in an ethylene dimerization or oligomerization reactor in presence of a dimerization or oligomerization catalyst to provide a first process stream. The $C_5+$ olefin stream is cracked in a cracking reactor under cracking conditions to provide a cracked stream comprising additional amounts of ethylene and propylene. The cracked stream is passed to the product separation zone to recover additional amounts of propylene. Finally, at least one of butene-1 and butadiene are recovered from the $C_4$ olefin stream.

In accordance with yet another exemplary embodiment, a process is provided for the production of propylene from an oxygenate feed comprising passing the oxygenate feed to an oxygenate-to-olefin reactor to contact the oxygenate feed with a catalyst comprising a silicoaluminophosphate (SAPO) to provide an effluent stream comprising light olefins comprising ethylene, propylene and butylene. The effluent stream is separated in a product separation zone to provide a propylene product stream, an ethylene stream, a $C_4+$ olefin stream and a $C_4+$ paraffin stream. The ethylene stream is reacted in an ethylene dimerization or oligomerization reactor in presence of a dimerization or oligomerization catalyst to provide a first process stream. The $C_4+$ olefin stream, the $C_4+$ paraffin stream and the first process stream are cracked in a cracking reactor under cracking conditions to provide a cracked stream comprising additional amounts of ethylene and propylene. Finally, the cracked stream is passed to the product separation zone to recover additional amounts of propylene.

These and other features, aspects, and advantages of the present disclosure will become better understood upon consideration of the following detailed description, drawings and appended claims.

BRIEF DESCRIPTION OF THE DRAWINGS

The various embodiments will hereinafter be described in conjunction with the following FIGURES, wherein like numerals denote like elements.

DEFINITIONS

Figure 1:
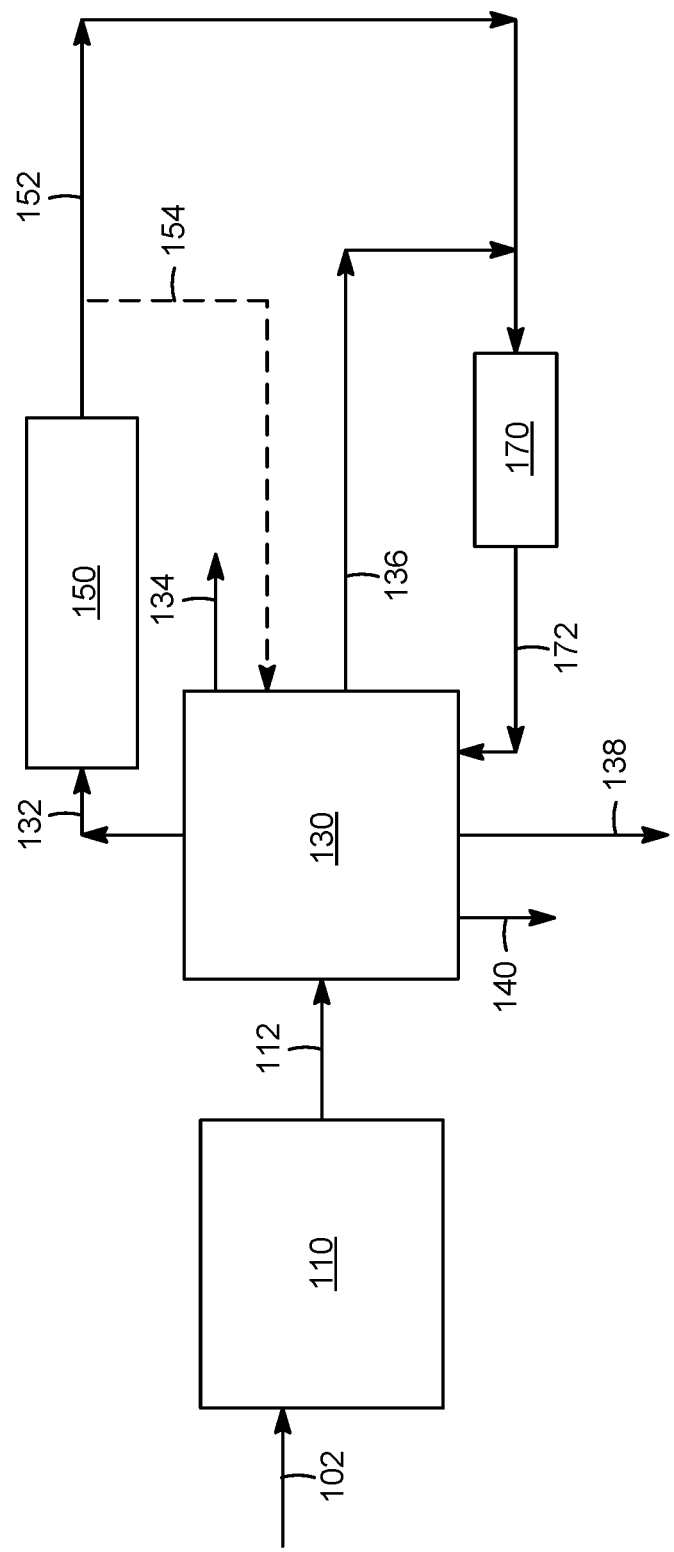
FIG. 1 is a schematic diagram of a process and an apparatus for the production of propylene in accordance with an exemplary embodiment.

As used herein, the term "stream" can include various hydrocarbon molecules and other substances.

The notation "Cx" means hydrocarbon molecules that have "x" number of carbon atoms, Cx+ means hydrocarbon molecules that have "x" and/or more than "x" number of carbon atoms, and Cx– means hydrocarbon molecules that have "x" and/or less than "x" number of carbon atoms.

As used herein, the term "stream" can include various hydrocarbon molecules, such as straight-chain, branched, or cyclic alkanes, alkenes, alkadienes, and alkynes, and optionally other substances, such as gases, e.g., hydrogen, or impurities, such as heavy metals, and sulfur and nitrogen compounds. The stream can also include aromatic and nonaromatic hydrocarbons. Moreover, the hydrocarbon molecules may be abbreviated C1, C2, C3 . . . Cn where "n" represents the number of carbon atoms in the one or more hydrocarbon molecules. Furthermore, a superscript "+" or "−" may be used with an abbreviated one or more hydrocarbons notation, e.g., C3+ or C3−, which is inclusive of the abbreviated one or more hydrocarbons. As an example, the abbreviation "C3+" means one or more hydrocarbon molecules of three or more carbon atoms. Also, the term "stream" can include or consist of other fluids, such as a hydrogen. Also, the symbol "A" in conjunction with a numeral and/or a superscript plus or minus may be used below to represent one or more aromatic compounds. As an example, the abbreviation "A9" may represent one or more aromatic C9 hydrocarbons.

As used herein, the term "zone" can refer to an area including one or more equipment items and/or one or more sub-zones. Equipment items can include one or more reactors or reactor vessels, heaters, exchangers, pipes, pumps, compressors, controllers and columns. Additionally, an equipment item, such as a reactor, dryer, or vessel, can further include one or more zones or sub-zones.

The term "light olefins" means the hydrocarbon material boiling in the range less than 38° C. atmospheric equivalent boiling point (AEBP) as determined by any standard gas chromatographic simulated distillation method such as ASTM D2887, all of which are used by the petroleum industry. The term "light olefins" includes $C_2$, $C_3$, and $C_4$ olefins.

As depicted, process flow lines in the FIGURES can be referred to interchangeably as, e.g., lines, pipes, feeds, gases, products, discharges, parts, portions, or streams.

The term "column" means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottom stream back to the bottom of the column. Feeds to the columns may be preheated. The top pressure is the pressure of the overhead vapor at the outlet of the column. The bottom temperature is the liquid bottom outlet temperature. Overhead lines and bottom lines refer to the net lines from the column downstream of the reflux or reboil to the column.

As used herein, the term "predominantly" means a majority, suitably at least 80 wt % and preferably at least 90 wt %.

As used herein, the term "minor amounts" means a small quantity, suitably less than about 10%, preferably less than about 5%, and optimally less than about 1%, by weight, of a compound or class of compounds in a stream.

As used herein, the term "passing" includes "feeding" and means that the material passes from a conduit or vessel to an object.

As used herein, the term "substantially" can mean an amount of at least generally about 80%, preferably about 90%, and optimally about 99%, by weight, of a compound or class of compounds in a stream.

DETAILED DESCRIPTION

The following detailed description is merely exemplary in nature and is not intended to limit the various embodiments or the application and uses thereof. Furthermore, there is no intention to be bound by any theory presented in the preceding background or the following detailed description. It will be appreciated by one skilled in the art that various features of the above described process, such as pumps, instrumentation, heat-exchange and recovery units, condensers, compressors, flash drums, feed tanks, and other ancillary or miscellaneous process equipment that are traditionally used in commercial embodiments of hydrocarbon conversion processes have not been described or illustrated. It will be understood that such accompanying equipment may be utilized in commercial embodiments of the flow schemes as described herein. Such ancillary or miscellaneous process equipment can be obtained and designed by one skilled in the art without undue experimentation.

The present invention provides an integrated MTO synthesis and ethylene oligomerization system. The integration of a MTO system, including its complementary olefin cracking reactor, with an ethylene oligomerization system facilitates increased overall selectivity to propylene. Further, the process and apparatus can be optionally used for producing a $C_4$ olefin product for its conversion to other high value-added products, such as butadiene, butene-1, as explained in more detail below.

An embodiment of a process for the production of light olefins is addressed with reference to a process and apparatus providing integration of ethylene oligomerization into an MTO-OCP for maximizing propylene production as shown in FIG. 1. The apparatus and method includes an oxygenate-to-olefin (OTO) reactor 110, a product separation zone 130, an ethylene oligomerization reactor 150 and a cracking reactor 170. In accordance with an exemplary embodiment as shown in FIG. 1, an oxygenate feed in line 102 may be passed to the oxygenate-to-olefin reactor 110. While the feedstock to the OTO reactor 110 may contain one or more aliphatic-containing compounds that include alcohols, amines, carbonyl compounds for example aldehydes, ketones and carboxylic acids, ethers, halides, mercaptans, sulfides, and mixtures thereof; it generally will be composed of a purified stream of light oxygenates such as one or more of methanol, ethanol, dimethyl ether, diethyl ether, or combinations thereof. In accordance with an exemplary embodiment as discussed, the oxygenate feed in line 102 may be methanol and may be referred to as the methanol feed. Accordingly, the oxygenate-to-olefin (OTO) reactor 110 is a Methanol to Olefin (MTO) reactor 110 for the purpose of discussion of the instant embodiment. In the MTO reactor 110, the methanol feed in line 102 contacts a catalyst comprising a silicoaluminophosphate (SAPO) under conditions designed to convert the methanol feed into predominately light olefins.

In general, the process for converting an oxygenate feedstock in the presence of a molecular sieve catalyst can be carried out in a variety of reactors, including as representative examples a fixed bed process, a fluidized bed process (includes a turbulent bed process), a continuous fluidized bed process, and a continuous high velocity fluidized bed process.

Reaction conditions for the conversion of oxygenates to light olefins are known to those skilled in the art. Preferably, in accordance with various embodiments, reaction conditions comprise a temperature between about 200° and about 700° C., more preferably between about 300° and 600° C., and most preferably between about 400° and about 550° C. As will be appreciated by those skilled in the art and guided by the teachings herein provided, the reactions conditions are generally variable such as dependent on the desired products. For example, in accordance with various embodiment discussed here for increased propylene production, operation at a reactor temperature between about 350° and about 475° C. and more preferably between about 400° and about 430° C. may be preferred.

A non-limiting list of suitable SAPO catalysts includes SAPO-5, SAPO-17, SAPO-18, SAPO-34, SAPO-35, SAPO-44, and mixtures thereof. The equipment and conditions with which this conversion reaction is conducted are well known to those skilled in the art and do not need to be detailed here. Numerous patents describe this process for various types of these catalysts including U.S. Pat. No. 3,928,483; U.S. Pat. No. 4,025,575; U.S. Pat. No. 4,252,479; U.S. Pat. No. 4,496,786; U.S. Pat. No. 4,547,616; U.S. Pat. No. 4,677,242; U.S. Pat. No. 4,843,183; U.S. Pat. No. 4,499,314; U.S. Pat. No. 4,447,669; U.S. Pat. No. 5,095,163; U.S. Pat. No. 5,191,141; U.S. Pat. No. 5,126,308; U.S. Pat. No. 4,973,792; and U.S. Pat. No. 4,861,938, the disclosures of which are incorporated herein by reference.

An effluent stream in line 112 comprising light olefins comprising ethylene, propylene and butylene may be withdrawn from the MTO reactor 110. In accordance with various embodiments, in addition to light olefins, the effluent stream in line 112 from the MTO reactor 110 may also typically include methane, ethane, propane, DME, $C_4$ saturates, $C_5$+ hydrocarbons, water and other hydrocarbon components in minor amounts. The effluent stream in line 112 may be passed to the product separation zone 130. In accordance with an exemplary embodiment, the effluent stream in line 112 may be separated in the product separation zone 130 to generate an ethylene stream in line 132, a propylene product stream in line 134 and a $C_4$+ stream in line 136. In accordance with various embodiments, the $C_4$+ stream in line 136 may comprise of $C_4$+ olefins and $C_4$+ paraffins. In an aspect, the $C_4$+ stream in line 136 predominantly comprises $C_4$+ olefins and minor amounts of $C_4$+ paraffins. Additionally, a bottoms stream in line 138 comprising $C_4$-$C_6$ paraffins and heavier hydrocarbons and a water stream in line 140 may be withdrawn from the product separation zone 130.

The ethylene stream in line 132 may be passed to the ethylene oligomerization reactor 150. In various embodiments, the ethylene oligomerization reactor may be an ethylene dimerization reactor and hence may be referred to as the ethylene dimerization reactor 150. The ethylene stream in line 132 may be reacted in the ethylene oligomerization or dimerization reactor 150 in presence of a dimerization or oligomerization catalyst to provide a first process stream in line 152. In various embodiments, the oligomerization or dimerization catalyst comprises a zeolite, wherein the zeolite may have a structure selected from the group consisting of MFI, MEL, ITH, IMF, TUN, FER, BEA, FAU, BPH, MEI, MSE, MWW, UZM-8, MOR, OFF, MTW, TON, MTT, AFO, ATO, and AEL, and mixtures thereof. In accordance with an exemplary embodiment, the dimerization or oligomerization catalyst comprises a solid phosphoric acid catalyst.

The first process stream in line 152 may be passed to the cracking reactor 170. In various embodiments, when the ethylene oligomerization reactor 150 is the ethylene dimerization reactor, a first portion comprising $C_4$ olefins in line 154 of the first process stream may be taken and passed to the product separation zone 130 with the remaining second portion in line 152 being passed to the cracking reactor 170.

As shown in FIG. 1, the $C_4$+ stream in line 136 and at least a portion of the first process stream in line 152 may be cracked in the cracking reactor 170 under cracking conditions in presence of a cracking catalyst to provide a cracked stream in line 172 comprising an additional amounts of ethylene and propylene. In the cracking reactor 170, $C_4+$ olefins present in $C_4+$ stream and the first process stream may be cracked to provide the additional amounts of ethylene and propylene. In various embodiments, $C_4+$ paraffins present in the $C_4+$ stream may be cracked to provide the additional amounts of ethylene and propylene.

Catalysts suitable for cracking comprise a crystalline silicate of the MFI family which may be a zeolite, a silicalite or any other silicate in that family or the MEL family which may be a zeolite or any other silicate in that family. Examples of MFI silicates are ZSM-5 and Silicalite. An example of an MEL zeolite is ZSM-11 which is known in the art. Other examples are Boralite D and Silicalite-2 as described by the International Zeolite Association, Atlas of Zeolite Structure Types, (Butterworths, 1987). The preferred crystalline silicates have pores or channels defined by ten oxygen rings and a high silicon/aluminum atomic ratio typically of at least 120 attained by suitable dealumination methods.

Suitable cracking conditions for cracking olefins include a temperature of around 400° to 650° C., preferably from 475° C. to about 650° C., yet more preferably 500° C. to about 625° C., and an olefin partial pressure of from 10 to 202 kPa absolute (1.5 to 29 psia), preferably from 50 to 152 kPa absolute (7 to 22 psia).

In accordance with an exemplary embodiment as shown in FIG. 1, an additional stream (not shown) comprising at least one of paraffins and olefins may be introduced to the cracking reactor 170 to produce additional propylene. The additional stream may be provided from any external source as long as it comprises required olefins and paraffins to augment the production of propylene in the instant process.

The cracked stream in line 172 may be passed to the product separation zone 130 to recover additional amounts of propylene obtained in the propylene product stream in line 134. It is an advantage of the instant process flow scheme as described that a substantially all of the ethylene is converted to propylene. An overall selectivity of as high as about 85% to propylene was achieved by the instant process and apparatus providing integration of ethylene oligomerization into an MTO-OCP flow scheme.

Figure 2A:
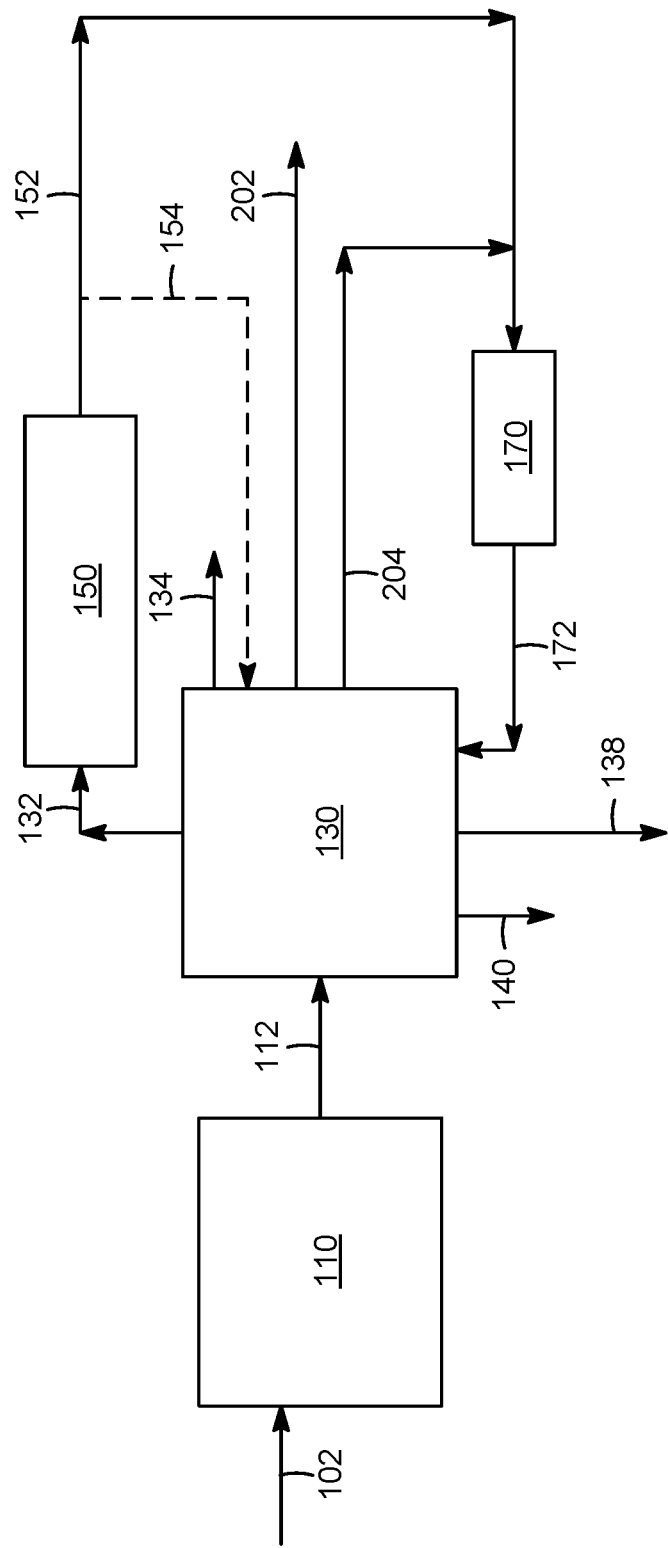
FIG. 2A is a schematic diagram of a process and an apparatus for the production of propylene in accordance with another exemplary embodiment.

Turning now to FIG. 2A, another embodiment for the production of light olefins is addressed with reference to a process and apparatus providing integration of ethylene oligomerization into an MTO-OCP for maximizing propylene production as shown in FIG. 2A. Additionally, the instant embodiment as discussed provides $C_4$ olefin product for its conversion to other high-value products, such as butadiene, butene-1. Many of the elements in FIG. 2A have the same configuration as in FIG. 1 and bear the same respective reference number and have similar operating conditions. Further, the temperature, pressure and composition of various streams are similar to the corresponding streams in FIG. 1, unless specified otherwise. As illustrated in the instant FIG. 2A, the effluent stream in line 112 from the MTO reactor 110 may be passed to the product separation zone 130 to separate the effluent stream to provide the ethylene stream in line 132, the propylene product stream in line 134, a $C_4$ olefin stream in line 202 and a $C_5+$ olefin stream in line 204. In various embodiments, the $C_4$ olefin stream in line 202 may comprise minor amounts of $C_4$ paraffin. In accordance with an exemplary embodiment as shown in FIG. 2A, the $C_5+$ olefin stream in line 204 may be passed to the cracking reactor 170 and processed further as discussed above with respect to FIG. 1. The $C_4$ olefin stream in line 202 is further processed to recover at least one of butene-1 and butadiene from the $C_4$ olefin stream as discussed with respect to FIG. 2B below.

Figure 2B:
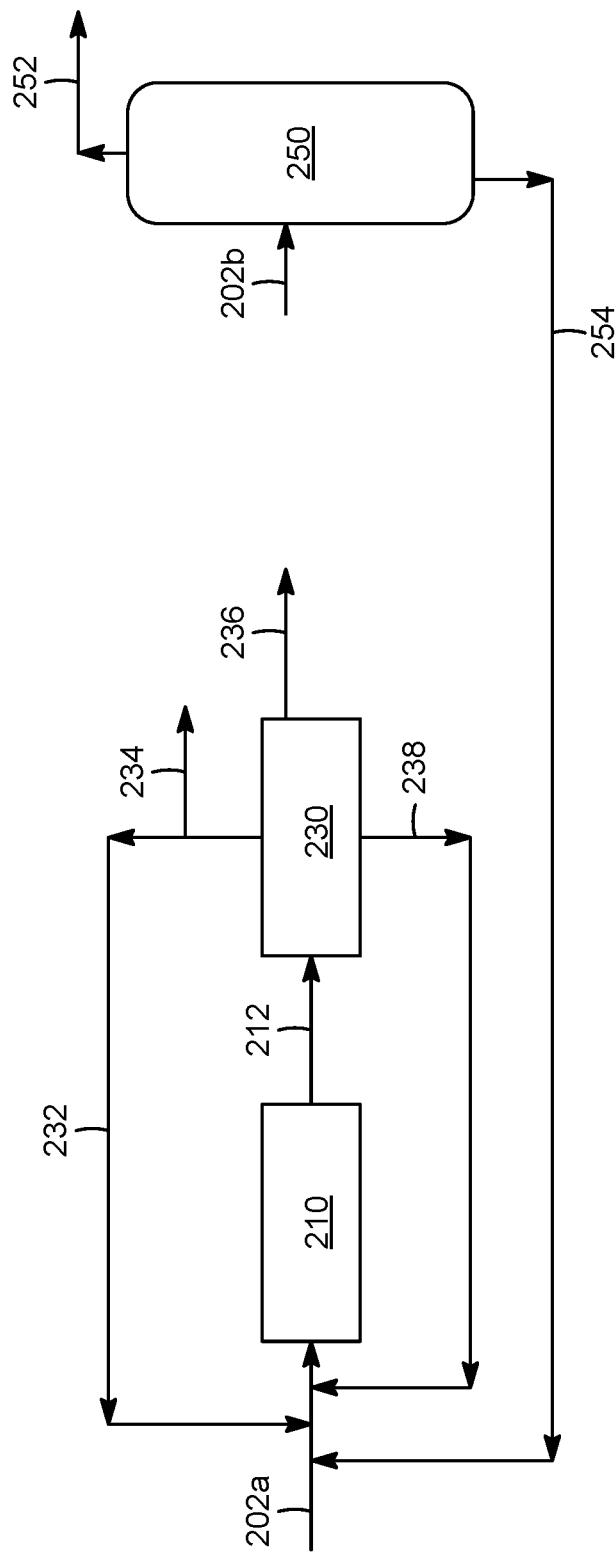
FIG. 2B is a schematic diagram of a process and an apparatus for conversion of $C_4$ olefin product to other high-value products in accordance with an exemplary embodiment.

Turning now to FIG. 2B, the figure illustrates a method and apparatus for conversion of $C_4$ olefin product to other high-value products in accordance with an exemplary embodiment. The apparatus and method includes a dehydrogenation reactor 210, a product recovery zone 230 and a separation zone 250. In accordance with an exemplary embodiment as shown in FIG. 2B, a first portion of the $C_4$ olefin stream in line 202a obtained from the $C_4$ olefin stream in line 202 may be provided to the dehydrogenation reactor 210. As shown, a second portion of $C_4$ olefin stream in line 202b may be provided to the separation zone 250.

The first portion of the $C_4$ olefin stream in line 202a may be contacted with a dehydrogenation catalyst in the dehydrogenation reactor 210 under dehydrogenation conditions provide a dehydrogenation effluent stream in line 212 comprising butadiene, hydrogen and unconverted $C_4$ olefins. The dehydrogenation effluent stream in line 212 may be passed to the product recovery zone 230 for separation. A butadiene product stream in line 236 is withdrawn from the product recovery zone 230. Further, a recycle hydrogen gas stream in line 232 and an unconverted $C_4$ olefin stream in line 238 may be withdrawn from the product recovery zone 230. In accordance with an exemplary embodiment as shown in FIG. 1, the recycle hydrogen gas stream in line 232 and the unconverted $C_4$ olefin stream in line 238 may be passed to the dehydrogenation reactor 210 in addition to the first portion of the $C_4$ olefin stream. Additionally, a hydrogen gas stream in line 234 may be taken out for use in other processes.

The second portion of the $C_4$ olefin stream in line 202b may undergo separation in the separation zone 250 to provide a butene-1 stream in line 252 and 2-butene stream in line 254. In accordance with an exemplary embodiment as shown in FIG. 2B, the 2-butene stream in line 254 may be passed to the dehydrogenation reactor 210 for further processing as discussed above to generate butadiene.

Specific Embodiments

While the following is described in conjunction with specific embodiments, it will be understood that this description is intended to illustrate and not limit the scope of the preceding description and the appended claims.

A first embodiment of the invention is a process for the production of propylene from an oxygenate feed, comprising passing the oxygenate feed to an oxygenate-to-olefin reactor to contact the oxygenate feed with a catalyst comprising a silicoaluminophosphate (SAPO) to provide an effluent stream comprising light olefins comprising ethylene, propylene and butylene; separating the effluent stream in a product separation zone to generate a propylene product stream, an ethylene stream and a $C_4+$ stream; reacting the ethylene stream in an ethylene dimerization or oligomerization reactor in presence of a dimerization or oligomerization catalyst to provide a first process stream; cracking the $C_4+$ stream and the first process stream in a cracking reactor under cracking conditions to provide a cracked stream comprising additional amounts of ethylene and propylene; and passing the cracked stream to the product separation zone to recover additional amounts of propylene. An embodiment of the invention is one, any or all of prior embodiments in this paragraph up through the first embodiment in this paragraph, wherein the SAPO catalyst is selected from the group consisting of SAPO-34, SAPO-18, SAPO-5 and mixtures thereof. An embodiment of the invention is one, any or all of prior embodiments in this paragraph up through the first embodiment in this paragraph, wherein the oxygenate feed comprise at least one of alcohols, aldehydes and ethers. An embodiment of the invention is one, any or all of prior embodiments in this paragraph up through the first embodiment in this paragraph further comprising introducing an additional stream comprising at least one of paraffins and olefins, to the cracking reactor. An embodiment of the invention is one, any or all of prior embodiments in this paragraph up through the first embodiment in this paragraph, wherein the $C_4+$ stream comprises at least one of $C_4+$ olefins and $C_4+$ paraffins and the step of cracking comprises cracking at least one of the $C_4+$ olefins and $C_4+$ paraffins. An embodiment of the invention is one, any or all of prior embodiments in this paragraph up through the first embodiment in this paragraph, wherein the cracking conditions comprise a temperature in the range of about 475° C. to about 650° C. An embodiment of the invention is one, any or all of prior embodiments in this paragraph up through the first embodiment in this paragraph, wherein the dimerization or oligomerization catalyst comprises a solid phosphoric acid catalyst. An embodiment of the invention is one, any or all of prior embodiments in this paragraph up through the first embodiment in this paragraph, wherein the dimerization or oligomerization catalyst comprises a zeolite, wherein the zeolite has a structure selected from the group consisting of MEI, MEL, ITH, IMF, TUN, FER, BEA, FAU, BPH, MEI, MSE, MWW, UZM-8, MOR, OFF, MTW, TON, MTT, AFO, ATO, and AEL, and mixtures thereof. An embodiment of the invention is one, any or all of prior embodiments in this paragraph up through the first embodiment in this paragraph, wherein the dimerization or oligomerization reactor is an oligomerization reactor. An embodiment of the invention is one, any or all of prior embodiments in this paragraph up through the first embodiment in this paragraph further comprising separating the $C_4+$ stream to a $C_4$ stream and a $C_5+$ stream; and passing the $C_5+$ stream to the cracking reactor. An embodiment of the invention is one, any or all of prior embodiments in this paragraph up through the first embodiment in this paragraph further comprising recovering at least one of butene-1 and butadiene from the $C_4$ stream. An embodiment of the invention is one, any or all of prior embodiments in this paragraph up through the first embodiment in this paragraph, wherein the step of recovering butadiene comprises contacting a first portion of the $C_4$ stream with a dehydrogenation catalyst in a dehydrogenation reaction zone under dehydrogenation conditions to form butadiene. An embodiment of the invention is one, any or all of prior embodiments in this paragraph up through the first embodiment in this paragraph, wherein the step of recovering butene-1 comprising separating a second portion of the $C_4$ stream to generate a butene-1 stream and a 2-butene stream. An embodiment of the invention is one, any or all of prior embodiments in this paragraph up through the first embodiment in this paragraph further comprising passing the 2-butene stream to the dehydrogenation reactor.

A second embodiment of the invention is a process for the production of propylene from an oxygenate feed, comprising passing the oxygenate feed to an oxygenate-to-olefin reactor to contact the oxygenate feed with a catalyst comprising a silicoaluminophosphate (SAPO) to provide an effluent stream comprising light olefins comprising ethylene, propylene and butylene; separating the effluent stream in a product separation zone to provide a propylene product stream, an ethylene stream, $C_4$ olefin stream and a $C_5+$ olefin stream; reacting the ethylene stream in an ethylene dimerization or oligomerization reactor in presence of a dimerization or oligomerization catalyst to provide a first process stream; cracking the $C_5+$ olefin stream in a cracking reactor under cracking conditions to provide a cracked stream comprising additional amounts of ethylene and propylene; passing the cracked stream to the product separation zone to recover additional amounts of propylene; recovering at least one of butene-1 and butadiene from the $C_4$ olefin stream. An embodiment of the invention is one, any or all of prior embodiments in this paragraph up through the second embodiment in this paragraph further comprising passing the first process stream to the cracking reactor. An embodiment of the invention is one, any or all of prior embodiments in this paragraph up through the second embodiment in this paragraph further comprising passing a first portion of the first process stream to the product separation zone and a second portion of the first process stream to the cracking reactor, wherein the first portion is between 1% and 99%, and the second portion is the remainder of the first process stream. An embodiment of the invention is one, any or all of prior embodiments in this paragraph up through the second embodiment in this paragraph, wherein the step of recovering comprises contacting a first portion of the $C_4$ olefin stream with a dehydrogenation catalyst in a dehydrogenation reaction zone under dehydrogenation conditions to form butadiene. An embodiment of the invention is one, any or all of prior embodiments in this paragraph up through the second embodiment in this paragraph, wherein the step of recovering comprising separating a second portion of the $C_4$ olefin stream to generate a butene-1 stream and a 2-butene stream and passing the 2-butene stream to the dehydrogenation reactor.

A third embodiment of the invention is a process for the production of propylene from an oxygenate feed, comprising a) passing the oxygenate feed to an oxygenate-to-olefin reactor to contact the oxygenate feed with a catalyst comprising a silicoaluminophosphate (SAPO) to provide an effluent stream comprising light olefins comprising ethylene, propylene and butylene and paraffins; b) separating the effluent stream in a product separation zone to provide a propylene product stream, an ethylene stream, a $C_4+$ olefin stream and a $C_4+$ paraffin stream; c) reacting the ethylene stream in an ethylene dimerization or oligomerization reactor in presence of a dimerization or oligomerization catalyst to provide a first process stream; d) cracking the $C_4+$ olefin stream, the $C_4+$ paraffin stream and the first process stream in a cracking reactor under cracking conditions to provide a cracked stream comprising additional amounts of ethylene and propylene; and e) passing the cracked stream to the product separation zone to recover additional amounts of propylene.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. An integrated process for the production of propylene from an oxygenate feed, comprising:
   (a) passing the oxygenate feed to an oxygenate-to-olefin reactor to contact the oxygenate feed with a catalyst comprising a silicoaluminophosphate (SAPO) to provide an effluent stream comprising light olefins comprising ethylene, propylene and butylene;
   (b) separating the effluent stream in a product separation zone to generate a propylene product stream, an ethylene stream and a $C_4+$ stream;
   (c) reacting the ethylene stream in an ethylene dimerization or oligomerization reactor in presence of a dimerization or oligomerization catalyst to provide a first process stream;
   (d) cracking the $C_4+$ stream and the first process stream in a cracking reactor under cracking conditions to provide a cracked stream comprising additional amounts of ethylene and propylene; and
   (e) passing the cracked stream to the product separation zone to recover additional amounts of propylene.

2. The process of claim 1, wherein the SAPO catalyst is selected from the group consisting of SAPO-34, SAPO-18, SAPO-5 and mixtures thereof.

3. The process of claim 1, wherein the oxygenate feed comprise at least one of alcohols, aldehydes and ethers.

4. The process of claim 1 further comprising introducing an additional stream comprising at least one of paraffins and olefins, to the cracking reactor.

5. The process of claim 1, wherein the $C_4+$ stream comprises at least one of $C_4+$ olefins and $C_4+$ paraffins and the step of cracking comprises cracking at least one of the $C_4+$ olefins and $C_4+$ paraffins.

6. The process of claim 5, wherein the cracking conditions comprise a temperature in the range of about 475° C. to about 650° C.

7. The process of claim 1, wherein the dimerization or oligomerization catalyst comprises a solid phosphoric acid catalyst.

8. The process of claim 1, wherein the dimerization or oligomerization catalyst comprises a zeolite, wherein the zeolite has a structure selected from the group consisting of MFI, MEL, ITH, IMF, TUN, FER, BEA, FAU, BPH, MEI, MSE, MWW, UZM-8, MOR, OFF, MTW, TON, MTT, AFO, ATO, and AEL, and mixtures thereof.

9. The process of claim 1, wherein the dimerization or oligomerization reactor is an oligomerization reactor.

10. The process of claim 1 further comprising:
    separating the $C_4+$ stream to a $C_4$ stream and a $C_5+$ stream; and
    passing the $C_5+$ stream to the cracking reactor.

11. The process of claim 10 further comprising recovering at least one of butene-1 and butadiene from the $C_4$ stream.

12. The process of claim 11, wherein the step of recovering butadiene comprises contacting a first portion of the $C_4$ stream with a dehydrogenation catalyst in a dehydrogenation reaction zone under dehydrogenation conditions to form butadiene.

13. The process of claim 11, wherein the step of recovering butene-1 comprising separating a second portion of the $C_4$ stream to generate a butene-1 stream and a 2-butene stream.

14. The process of claim 13 further comprising passing the 2-butene stream to the dehydrogenation reactor.

15. An integrated process for the production of propylene from an oxygenate feed, comprising:
    (a) passing the oxygenate feed to an oxygenate-to-olefin reactor to contact the oxygenate feed with a catalyst comprising a silicoaluminophosphate (SAPO) to provide an effluent stream comprising light olefins comprising ethylene, propylene and butylene;
    (b) separating the effluent stream in a product separation zone to provide a propylene product stream, an ethylene stream, $C_4$ olefin stream and a $C_5+$ olefin stream;
    (c) reacting the ethylene stream in an ethylene dimerization or oligomerization reactor in presence of a dimerization or oligomerization catalyst to provide a first process stream;
    (d) cracking the $C_5+$ olefin stream in a cracking reactor under cracking conditions to provide a cracked stream comprising additional amounts of ethylene and propylene;
    (e) passing the cracked stream to the product separation zone to recover additional amounts of propylene; and
    (f) recovering at least one of butene-1 and butadiene from the $C_4$ olefin stream.

16. The process of claim 15 further comprising passing the first process stream to the cracking reactor.

17. The process of claim 15 further comprising passing a first portion of the first process stream to the product separation zone and a second portion of the first process stream to the cracking reactor, wherein the first portion is between 1% and 99%, and the second portion is the remainder of the first process stream.

18. The process of claim 15, wherein the step of recovering comprises contacting a first portion of the $C_4$ olefin stream with a dehydrogenation catalyst in a dehydrogenation reaction zone under dehydrogenation conditions to form butadiene.

19. The process of claim 15, wherein the step of recovering comprising separating a second portion of the $C_4$ olefin stream to generate a butene-1 stream and a 2-butene stream and passing the 2-butene stream to the dehydrogenation reactor.

20. An integrated process for the production of propylene from an oxygenate feed, comprising:
    (a) passing the oxygenate feed to an oxygenate-to-olefin reactor to contact the oxygenate feed with a catalyst comprising a silicoaluminophosphate (SAPO) to provide an effluent stream comprising light olefins comprising ethylene, propylene and butylene and paraffins;
    (b) separating the effluent stream in a product separation zone to provide a propylene product stream, an ethylene stream, a $C_4+$ olefin stream and a $C_4+$ paraffin stream;
    (c) reacting the ethylene stream in an ethylene dimerization or oligomerization reactor in presence of a dimerization or oligomerization catalyst to provide a first process stream;
    (d) cracking the $C_4+$ olefin stream, the $C_4+$ paraffin stream and the first process stream in a cracking reactor under cracking conditions to provide a cracked stream comprising additional amounts of ethylene and propylene; and
    (e) passing the cracked stream to the product separation zone to recover additional amounts of propylene.

* * * * *